United States Patent
Norman

(10) Patent No.: US 8,981,172 B2
(45) Date of Patent: Mar. 17, 2015

(54) CATALYTIC DEHYDRATION OF ALCOHOLS AND ETHERS OVER A TERNARY MIXED OXIDE

(75) Inventor: David William Norman, Kingsport, TN (US)

(73) Assignee: Eastman Chemical Company, Kingsport, TN (US)

(*) Notice: Subject to any disclaimer, the term of this patent is extended or adjusted under 35 U.S.C. 154(b) by 21 days.

(21) Appl. No.: 13/234,277

(22) Filed: Sep. 16, 2011

(65) Prior Publication Data

US 2013/0072696 A1    Mar. 21, 2013

(51) Int. Cl.
```
C01C 1/20      (2006.01)
B01J 35/10     (2006.01)
B01J 27/198    (2006.01)
B01J 27/28     (2006.01)
C07C 1/24      (2006.01)
C07C 45/52     (2006.01)
B01J 37/03     (2006.01)
B01J 38/02     (2006.01)
B01J 23/00     (2006.01)
B01J 35/00     (2006.01)
B01J 35/02     (2006.01)
B01J 37/00     (2006.01)
```

(52) U.S. Cl.
CPC ............ B01J 35/1014 (2013.01); B01J 27/198 (2013.01); B01J 27/285 (2013.01); C07C 1/24 (2013.01); C07C 45/52 (2013.01); C07C 2521/06 (2013.01); C07C 2527/198 (2013.01); B01J 37/031 (2013.01); B01J 38/02 (2013.01); B01J 23/002 (2013.01); B01J 35/002 (2013.01); B01J 35/023 (2013.01); B01J 37/0036 (2013.01)
USPC ............ 585/638; 585/639; 585/640; 585/641

(58) Field of Classification Search
CPC .................................. C07C 1/20; C07C 47/22
USPC .......... 585/638, 639, 641, 642, 640; 502/209
See application file for complete search history.

(56) References Cited

U.S. PATENT DOCUMENTS

| | | | |
|---|---|---|---|
| 2,273,484 A | 2/1942 | Guinot | |
| 3,226,337 A | 12/1965 | Riemenschneider et al. | |
| 3,894,971 A | 7/1975 | Reuter et al. | |
| 4,151,116 A | 4/1979 | McDermott | |
| 4,250,346 A | 2/1981 | Thorsteinson et al. | |
| 4,382,876 A | 5/1983 | Neubold et al. | |
| 4,447,638 A | 5/1984 | Gaffney et al. | |
| 4,515,904 A | 5/1985 | Edwards | |
| 6,046,373 A * | 4/2000 | Sun ............... | 585/640 |
| 8,765,629 B2 * | 7/2014 | Norman et al. ........ | 502/209 |
| 2002/0183199 A1 * | 12/2002 | Bogan, Jr. ........... | 502/215 |
| 2004/0162217 A1 | 8/2004 | Alnonetti et al. | |
| 2010/0076233 A1 * | 3/2010 | Cortright et al. ......... | 585/251 |
| 2011/0160491 A1 | 6/2011 | Dubois et al. | |
| 2011/0213174 A1 | 9/2011 | Dubois | |
| 2013/0102455 A1 | 4/2013 | Haddad et al. | |
| 2013/0237724 A1 | 9/2013 | Boppana et al. | |

FOREIGN PATENT DOCUMENTS

| | | |
|---|---|---|
| DE | 1931720 A1 | 6/1970 |
| DE | 102004014932 A1 | 10/2004 |
| EP | 2340888 A1 | 7/2011 |
| GB | 589 709 | 6/1947 |
| JP | 5-017392 A | 1/1993 |

OTHER PUBLICATIONS

Mamoru, Effect of the Composition of Vanadium-Titanium Binary Phosphate on Catalytic Performance in Vapor-Phase Adol Condensation. Applied Catalysts, 54 (1989) pp. 29-36.*
Bartley, Jonathan K. et al.; "Chapter 12 Vanadium Phosphate Catalysts"; Metal Oxide Catalysis; 2009; pp. 499-537; Wiley-VCH Verlag GmbH & Co, KGaA, Weinheim.
Chatterjee, Maya et al.; "An attempt to achieve the direct hydrogenolysis of tetrahydrofurfuryl alcohol in supercritical carbon dioxide"; Catalysis Science & Technology 2011; DOI: 10.1039/c1cy00125f; retrieved from www.rsc.org/catalysis.
Chouikin, N. I. and Belski, I. F.; "No. 239—Catalytic Hydrogenolysis in the Series of Furan Compounds"; Mémoires Présentés a la Société Chimique; May 1956; pp. 1556-1560.
Geilen, Frank M. A. et al.; "Selective and Flexible Transformation of Biomass-Derived Platform Chemicals by a Multifunctional Catalytic System"; Angew. Chem. Int. Ed. 2010; 49; pp. 5510-5514; DOI: 10.1002/anie.201002060 retrieved from www.angewandte.org.
Reppe, W. et al.; "Description of Experiments—Dehydration of y-Alkanediols"; Justus Liebigs Annalen der Chemie; 1955; pp. 109-113.
Shuikin, N. I. and Tulupov, V. A.; "Possibility of Forming Cyclopentadiene from Heterocyclic Compounds Containing Five Carbon Atoms"; Izvestiya Akademii Nauk SSSR, Seriya Khimicheskaya; 1956; pp. 205-210.
Spivey, James J. et al.; "Vapor Phase Condensation Reactions Using Formaldehyde or Methanol"; Catalysis, vol. 12; 1996; pp. 152-198.
Al, M; "Preparation of high-surface-area titanium-vanadium binary pyrophosphate catalysts"; Applied Catalysis, vol. 48, No. 1, Mar. 1, 1989, pp. 51-61.
International Search Report received Jan. 2, 2013 for international application No. PCT/US2012/052989 filed Aug. 30, 2012.
Office Action notification dated Sep. 9, 2013 received in co-pending U.S. Appl. No. 13/234,313.

(Continued)

*Primary Examiner* — In Suk Bullock
*Assistant Examiner* — Sharon Pregler
(74) *Attorney, Agent, or Firm* — James K. Leonard; Jennifer R. Knight

(57) ABSTRACT

A ternary V—Ti—P mixed oxide is shown to catalytically dehydrate 2-methyl-tetrahydrofuran in high conversion to give piperylene, in good yield. Volatile products collected from this reaction contain piperylene in concentrations as high as 80 percent by weight. Dehydration of glycerol to acrolein in high conversion and moderate selectivity is also demonstrated. The catalyst is also shown to dehydrate other alcohols and ether substrates. The catalyst is resistant to deactivation and maintains activity between runs.

10 Claims, No Drawings

(56) References Cited

OTHER PUBLICATIONS

USPTO Notice of Allowance dated Mar. 10, 2014 for Co-pending U.S. Appl. No. 13/234,313.
Notification of Transmittal of the International Search Report and the Written Opinion of the International Searching Authority, or the Declaration—International Application No. PCT/US2014/020204 with a mailing date Jun. 10, 2014.
Otake, Masayuki; "Method for the Manufacture of Composite Oxide Catalyst"; English translation of JP S64-4817, Publication Date is Jan. 26, 1989.
Notice of Allowance dated Jul. 14, 2014 received in co-pending U.S. Appl. No. 13/234,323.

* cited by examiner

CATALYTIC DEHYDRATION OF ALCOHOLS AND ETHERS OVER A TERNARY MIXED OXIDE

FIELD OF THE INVENTION

This invention pertains to a process for the preparation of alkenes, dienes and aldehydes from alcohols and ethers which employ a vanadium-titanium-phosphorus mixed oxide catalyst.

BACKGROUND OF THE INVENTION

Geochemical processes have created energy dense non-renewable organic feedstocks by concentrating and dehydrating biological materials. The chemical industry has since developed elegant and efficient methods for exploiting this valuable, yet limited, resource. In the event that current processes become uneconomical, supplementing petrochemical production by converting renewable bio-based feedstocks to marketable products will grow in importance. However, removing up to 50 weight percent water from biological materials while maximizing product selectivity poses significant challenges to the research community. Piperylenes, for example, are by-products of the petroleum industry and are important raw materials for the manufacture of plastics, adhesives and resins. Due to process improvements that reduce by-product formation, commercial piperylenes supplies are increasingly becoming limited. Decoupling of piperylenes from the petroleum industry may therefore provide an advantaged route to this valuable product.

The major component of this C5 mixture is 1,3-pentadiene and is commonly referred to as piperylene; 1,4-pentadiene is a minor component and can be isomerized to the 1,3-isomer. Catalytic dehydration of 2-methyl-tetrahydrofuran (2-Me-THF), a bio-derived feedstock, may provide a competitive alternative route to 1,3-pentadiene. Coverage of this reaction by the prior art is limited and lacking specific examples; however, it is clear that an acidic catalyst is necessary to carry out this transformation. Various metal oxides, phosphate salts and titanium dioxide supported on alumina reportedly perform the dehydration reaction. For example, a boron phosphate catalyst has been reported to convert 40% of 2-Me-THF to 1,3-pentadiene with 91% selectivity to give a single pass yield of 36% and a space-time-yield (STY) of 3.1 moles 1,3-pentadiene/Kg catalyst/h.

Secondary reactions such as piperylene polymerization and generation of gaseous decomposition products lead to yield loss in this reaction. Catalyst coking can also hinder performance as well as catalyst sensitivity to reactants and products, which can lead to catalyst deactivation. A preferred catalyst for this reaction would therefore demonstrate high 2-Me-THF conversion and high selectivity to pentadiene and maintain activity between runs.

Dehydration of other substrates such as mono-alcohols can afford useful alkene products while di-alcohol and cyclic ether substrates can lead to the corresponding dienes. For example, n-pentanol is expected to form a mixture of linear pentenes while pentane diols would form a mixture of pentadiene isomers. Tetrahydropyran and 3-methyl-tetrahydrofuran, both cyclic ethers, are expected to form pentadiene isomers and isoprene, respectively.

It is known that tri-alcohol substrates such as glycerol, a bio-diesel co-product, can be converted into acrolein upon dehydration. This product is the immediate commercial precursor to acrylic acid but is very reactive and prone to polymerization, particularly on acidic catalyst surfaces. Formation of hydroxyacetone (acetol) and acetone are also possible products from this reaction. Thus, catalytic dehydration of glycerol to acrolein can pose significant selectivity challenges.

A catalyst capable of facilitating the aforementioned dehydration reactions, and that is reusable and does not deactivate in the presence of copious amounts of water would be very useful.

BRIEF SUMMARY OF THE INVENTION

A first aspect, the present invention provides a process for the dehydration of an oxygenated organic compound, comprising reacting the organic compound in the presence of a vanadium-titanium-phosphorus oxide catalyst to thereby dehydrate said organic compound.

DETAILED DESCRIPTION

According to an embodiment, the catalyst described herein is capable of facilitating the aforementioned dehydration reactions in It is reusable and does not deactivate in the presence of copious amounts of water.

Ternary vanadium phosphorus oxides (VPOs) composed of vanadium, titanium and phosphorus (V—Ti—P) are amphoteric catalysts and have been reported to produce acrylates in higher yield than the binary V—P analogues, but have not been studied for use in dehydration reactions. Thus, according to an embodiment, the invention disclosed herein concerns a process for producing unsaturated hydrocarbons and aldehydes via a vanadium-titanium-phosphorus (V—Ti—P) oxide catalyst. For example, it has been surprisingly found that the V—Ti—P catalyst not only demonstrates high conversion of 2-methyl-tetrahydrofuran but also produces piperylene in good yield and maintains activity between runs. Conversion of 2-Me-THF to piperylene provides an attractive alternative route to this valuable precursor molecule. In addition to offering a competitive substitute to the current petrochemical pathway, efficient catalysis of this dehydration reaction provides a more sustainable approach since 2-Me-THF is produced from bio-derived chemicals such as levulinic acid and furfural. By "piperylene" or "piperylenes", it is meant 1,3-pentadiene, 1,4-pentadiene or combinations thereof. As illustrated in the examples below, the V—Ti—P catalyst demonstrates a 2-Me-THF conversion as high as 95%, a selectivity to piperylene as high as 81%, a per pass piperylene yield as high as 65% and a STY up to 15 moles piperylene/Kg catalyst/h. Upon regeneration in air, the catalyst performance is completely reproducible. This suggests that the V—Ti—P material is resistant to deactivation by the organic reactant, products and the co-generated water.

Attempts to reproduce the 2-Me-THF performance of the previously disclosed boron phosphate catalyst were unsuccessful. The catalyst was prepared as described in the prior art, however, each experiment using this material led to high 2-Me-THF conversion but with little to no selectivity to piperylene. Indeed, using the reactor conditions described in the prior art gave essentially no piperylene. Upon removal from the reactor it was apparent that the catalyst and reactor tube were contaminated with extensive coke deposits, even after attempted regeneration in air at 400° C. The V—Ti—P catalyst on the other hand displays no visible evidence of coke formation upon similar treatment.

The V—Ti—P catalyst is also capable of converting other bio-derived chemicals to the corresponding dehydrated alkenes and dienes. For example, n-pentanol can be dehydrated at 100% conversion and in 81% selectivity to a mixture of linear and branched pentenes. 1,5-pentane diol can be dehydrated at 100% conversion to give piperylene in 38% selectivity and tetrahydropyran (THP) in 39% selectivity, which results from partial dehydration of the feed. As a substrate, THP is a more challenging cyclic ether to dehydrate over the V—Ti—P catalyst. It is less reactive than 2-Me-THF owing to the fact that it has inherently lower basicity. Nonetheless, THP can be converted to piperylene at 45% selectivity and at 44% conversion.

The majority of examples discussed below employ identical reaction conditions for the dehydration of various substrates. The reactor temperature, for example, was approximately 350° C. which was suitable for aiding in selective conversion of primary alcohol substrates such as n-pentanol and 1,5-pentane diol. Dehydrations of secondary alcohols, on the other hand, were considerably less selective even though the conversions were 100%. Secondary alcohols are typically more reactive than the primary congeners, thus, lower reactor temperatures can improve the selectivity in these dehydration reactions.

Glycerol dehydration to acrolein, an alpha,beta-unsaturated aldehyde, is known to occur via acid catalysis in both the liquid and vapor phase. This reaction is of interest because it offers a sustainable alternative to acrylic acid, which is currently manufactured by a two stage oxidation of propylene. The V—Ti—P catalyst can convert an aqueous solution of glycerol to acrolein in high conversion and moderate selectivity. Due to the secondary alcohol functional groups present in glycerol, the reactor temperature required to carry out this reaction is considerably lower than that of the previously discussed substrates. For example, when performed at 300° C. the glycerol conversion is 92% and the selectivity to acrolein is 56%, giving a per pass yield of 52% and a STY of 4 moles of acrolein/Kg catalyst/h.

According to an embodiment, the V—Ti—P catalyst employed in the dehydration reactions can be prepared according to many methods. However, typically, the catalyst is obtained by suspending a vanadium precursor such as ammonium metavanadate in water followed by addition of 85% phosphoric acid. This solution is then added to an aqueous solution of a water soluble titanium precursor (TBALDH). The resulting suspension is stirred at elevated temperature followed by water removal via distillation. Calcination of the resulting solid in air then provides the desired catalyst. The catalyst compositions have the general formula $VTi_aP_bO_c$, wherein a=0.3 to 6.0, preferably 1.0 to 4.0; b=2.0 to 13.0, preferably 4.0 to 10.0; and c is the number of atoms required to satisfy the valences of the components other than oxygen.

According to an embodiment, the process includes dehydration of an oxygenated organic compound containing at least 1 to 6 alcohol functional groups, at least 1 to 3 ether groups and at least 1 to 6 carbon atoms or combinations thereof. For example, such organic compounds could include ethanol, n-propanol, 1,3-propane diol, 1,2-propane diol, iso-propanol, 1,2,3-propane triol (glycerol), n-butanol, 1,4-butane diol, 1,3-butane diol, 1,2-butane diol, iso-butanol, tetrahydrofuran, dihyrdofuran, 1,2,3,4-butane tetrol (threitol, erythritol), n-pentanol, 1,5-pentane diol, 1,4-pentane diol, 1,3-pentane diol, 1,2-pentane diol, 2,4-pentane diol, cyclopentanol, cyclopentane diol, pentaerythritol, 1,2,3,4,5-pentane pentol (xylitol), tetrahydropyran, dihydropyran, 2-methyl-tetrahydrofuran, 3-methyl-tetrahydrofuran, 3-methyl-1,3,5-pentane triol, 1,6-hexane diol, 1,5-hexane diol, 2,5-hexane diol, 3-methyl-1,5-penta diol, hexylene glycol, pinacol, hexane triol, cyclohexanol, cyclohexane diol, methyltetrahydropyran, 1,2,3,4,5,6-hexane hexol (sorbitol). Functional groups such as ketones, lactones, aldehydes, esters and carboxylic acids may also be present in the substrate molecule. Additionally, heteroatoms other than oxygen such as nitrogen, phosphorus, sulfur may also be present in the substrate molecule.

According to an embodiment of the present invention, products which result from the process include ethylene, propylene, 1-butene, 2-butene, 2-methyl-propene, butadiene, 1-pentene, 2-pentene, 2-methyl-2-butene, 2-methyl-1-butene, 1,3-pentadiene, 1,4-pentadiene, isoprene, tetrahydropyran, cyclopentene, cyclopentadiene, 1-hexene, 2-hexene, 3-hexene, 4-methyl-1-pentene, 4-methyl-2-pentene, 2-methyl-1-pentene, 2-methyl-2-pentene, 3-methyl-2-pentene, 1,3-hexadiene, 1,4-hexadiene, 1,5-hexadiene, 2,4-hexadiene, methyltetrahydropyran, cyclohexene, cyclohexadiene, acetone, hydroxyacetone, acrolein. The organic compound is dehydrated over the V—Ti—P catalyst at a process temperature of from about 250° C. to about 500° C., from about 300° C. to about 450° C., or from about 325° C. to about 375° C. Moreover, an optional non-reactive carrier gas such as nitrogen or oxygen depleted air may be used from about 10 SCCM to 1000 SCCM, or from about 50 SCCM to 500 SCCM or from about 80 SCCM to 100 SCCM. The non-reactive carrier gas can be present at concentrations ranging from 0.1 to 90 mole % of the total feed, from 10 to 70 mole %, or even from 40 to 60 mole %. In addition, reactive gasses such as oxygen may also be introduced during the reaction to minimize the amount of coke build up. The concentration of the oxygen component can range from 0.1 to 25 mole %, from 1 to 15 mole %, or even from 2 to 5 mole %. In the event of coke deposition, the catalyst may be regenerated between reaction runs in air at a temperature of from about 300° C. to about 600° C.

The process can be run at a pressure from about 0.1 to about 100 bars absolute (bara), from about 1 to about 50 bara, or even from about 10 to about 20 bara.

According to an embodiment, the feed material for the dehydration reaction is an organic compound. If the organic compound is in liquid form at the desired feed temperature it may be mixed with diluents such as water. If the organic compound is solid at the desired feed temperature then it may be dissolved in aqueous or organic solvents. Moreover, according to an embodiment, the liquid feed rate for this reaction can be from about 1.0 to about 1000 mL/Kg catalyst/minute, from about 5 to about 500 mL/Kg/catalyst/minute, or from about 10 to 100 mL/Kg catalyst/minute. Inhibitors such as butylhydroxytoluene (BHT) may be added to the product to minimize polymerization.

EXAMPLES

Materials

Ammonium metavanadate (99+ wt % $NH_4VO_3$), phosphoric acid (85 wt % $H_3PO_4$), titanium(IV) bis(ammonium lactate)dihydroxide (50 wt. % solution in water), boric acid, and the alcohol and ether substrates were purchased from commercial suppliers and used as received.

Abbreviations

XRD=X-ray Diffraction; SCCM=standard cubic centimeters per minute; 2-Me-THF=2-Methyl-tetrahydrofuran; 3-Me-THF=3-Methyl-tetrahydrofuran; THP=tetrahydropyran; 3-Me-THP=3-Methyl-tetrahydropyran; 1,4-$C_5H_8$=1,4-Pentadiene; 1,3-$C_5H_8$=1,3-Pentadiene; STY=Space-Time-Yield.

Gas Chromatography Protocols

Liquid product samples were collected over a measured time period, weighed, and analyzed by gas chromatography.

Samples were weighed into a vial to a recorded weight of 1.0XXX g (where X is the actual number shown on the balance) along with 7.86 g of an internal standard solution. The internal standard solution was prepared by weighing 75.00 g of cyclopentanone into a 1000 mL flask then filling the flask to volume with acetonitrile. To separate all components, each sample was injected on a Shimadzu 2010 gas chromatograph calibrated to potential analytes. This protocol was used to analyze product from all dehydration reactions except those of glycerol.

Liquid product samples from glycerol dehydration were analyzed by weighing approximately 1.2 g of the sample into a GC vial along with about 0.15 g of THF as an internal standard. To separate all components, each sample was injected on a HP5890 gas chromatograph calibrated to potential analytes.

Example 1.

Vapor Phase Dehydration of 2-Methyl-THF over a V—Ti—P Catalyst at 300° C.

The catalyst was prepared by first suspending ammonium metavanadate (19.455 g) in 300 mL of deionized water in a 500 mL single necked round bottomed flask. After heating at 70° C. for 1 hour, 85% orthophosphoric acid (105.4 g) was added at 70° C. over a 15 minute period to give a light orange solution. Residual reactants were washed into the reaction flask with a minimal amount of water. The 50 wt. % titanium (IV) bis(ammonium lactato)dihydroxide (TBALDH) solution (218.45 g) was added to a 1 L three necked kettle reactor equipped with a condenser and a mechanical stirrer. The V/P solution was slowly poured into the TBALDH solution to give a pale green suspension. The V/P flask was rinsed with 30 mL of water and the contents added to the reaction flask. The mixture was then stirred at 700 to 800 rpm at 130° C. for 16 hours. The water was then removed via distillation over 4 to 6 h and the resulting damp pale green solid transferred to a ceramic dish and heated in air at 300° C. for 16 hours in a muffle furnace. The resulting solid was crushed and sieved to 8×14 mesh. The 8×14 mesh was then calcined for 6 hours at 450° C. in air (60 SCCM) in a quartz tube to give pale green irregular shaped pellets. This material has a BET surface area of 51.4 m$^2$/g, is amorphous via X-ray diffraction and has a molar composition of 1.0V-2.0Ti-5.1P, as determined by X-ray Fluorescence Spectroscopy.

The dehydration of 2-Methyl-THF was performed in a 25 mm outer diameter (21 mm inner diameter) quartz reactor tube with length=61 cm (24 inches). Heat to the reactor was provided by a Barnstead International electric tube furnace (type F21100). The quartz reactor had indentations 20 cm (8 inches) up from the base of the tube. The region of the reactor with the indentations was situated near the base of the heated section of the furnace. The reactor was also fitted with a thermowell that extended from the top of the reactor to about an inch below the indentations. The reactor was first loaded with quartz chips to about 2.5 inches in height above the indentations to allow the catalyst to be positioned in the middle of the furnace. The reactor was then loaded with a 5.0 g charge of catalyst. The thermocouple in the thermowell was placed near the center of the catalyst bed. Sufficient quartz chips (about 2.5 inches) were added to the region above the catalyst charge to reach the top of the heated region of the furnace. Liquid products were collected in a three necked flask fitted to dry ice condenser with trap. The base of the primary receiver flask and the dry ice trap were each fitted with a stopcock to allow for draining of the liquid products.

The dehydration reaction was performed using a nitrogen carrier gas set at 80 SCCM and an anhydrous 2-methyl-tetrahydrofuran feed rate of 0.2 mL/min. The furnace temperature was set to 300° C. Liquid samples were collected after a three hour time period, weighed and the organic products analyzed by gas chromatography (GC). The performance of the catalyst is summarized in Table 1. The weight percent analytical data of the organic components of the samples are summarized in Table 2. Biphasic material collected in the primary receiver is labeled 'Receiver'; anhydrous tetrahydrofuran was added to homogenize the sample prior to GC analysis. Material collected from the dry ice trap receiver thirty minutes after run completion is labeled 'Trap 1'. Material collected from the dry ice trap receiver upon warming of the trap to room temperature is labeled 'Trap 2'; anhydrous tetrahydrofuran was added to homogenize the sample prior to GC analysis.

This example shows that the V—Ti—P catalyst is active for the dehydration of 2-Me-THF to piperylene. Nearly 60% of the substrate is converted and the product selectivities to 1,4- and 1,3-pentadiene are about 10% and 60%, respectively. The STY, or rate, of this reaction is 8.6 moles 1,3-pentadiene/Kg catalyst/h.

Example 2:

Vapor Phase Dehydration of 2-Methyl-THF over a V—Ti—P Catalyst at 350° C.

The dehydration reaction in this example was performed in accordance with Example 1 except that the catalyst was regenerated prior to the run at 400° C. with an air flow of 128 SCCM for 16 hours. The furnace temperature was then adjusted to 350° C. and the carrier gas changed to nitrogen (80 SCCM). The performance of the catalyst is summarized in Table 1. The weight percent analytical data of the organic components of the samples are summarized in Table 2. This example shows that the 2-Me-THF conversion (88%) is higher at this reactor temperature and the selectivity to 1,3-pentadiene is increased to 66% while the selectivity to 1,4-pentadiene is lowered to 5.5%. The overall per pass yield of this reaction to 1,3-pentadiene is about 59% and the rate is 14 moles 1,3-pentadiene/Kg catalyst/h.

Example 3:

Reproducibility of Example 2 Reactor Conditions

The dehydration reaction in this example was performed in accordance with Example 2 except that 0.02 g of BHT inhibitor was added to the sample vials. The performance of the catalyst is summarized in Table 1. The weight percent analytical data of the organic components of the samples are summarized in Table 2. This example clearly shows that the V—Ti—P catalyst performance is completely reproducible after regeneration in air. The same 2-Me-THF conversion (88%) is observed and the selectivity to 1,3-pentadiene, 1,4-pentadiene and the high production rate are essentially the same as those described in the previous example. The sum concentration of 1,3- and 1,4-pentadiene in the volatile fraction (Trap 2) is approximately 82 percent by weight.

Example 4:

Lifetime Study of 2-Me-THF Dehydration to Piperylenes

The dehydration reaction in this example was performed in accordance with Example 2 except that the reaction ran for eight hours. Liquid samples were taken at two, four, six and eight hours. The performance of the catalyst is summarized in Table 3. This example shows that after the initial data point, the selectivity toward piperylenes holds steady around 80% but the conversion gradually decreases with time, presumably due to coke formation. Co-feeding small amounts of oxygen may be advantageous in this process since the coke would combust upon formation thereby maintaining constant activity.

Comparative Example 1:

2-Me-THF Dehydration using a Boron Phosphate Catalyst

The catalyst in this example was prepared as described in the prior art by mixing 61.83 g of boric acid and 115.29 g of 85 wt. % phosphoric acid and 100 g of deionized water in a 500 mL beaker. After two hours of mechanical stirring the white paste was transferred to a ceramic dish and dried at 110° C. for 16 hours. The white solid was then crushed and sieved to 8×14 mesh and calcined at 350° C. for 3 hours under a 100 SCCM air flow. Five grams of this material was then charged to a quartz reactor tube. The dehydration of 2-Me-THF was carried out as described in Example 2. The performance of the catalyst is summarized in Table 1. This example shows that, under identical reactor conditions, the boron phosphate catalyst produces piperylene in less than half the selectivity of the V—Ti—P catalyst. Moreover, the material balance of the reaction is 77% while that of the V—Ti—P catalyzed reaction is 94% indicating extensive feed decomposition to coke or gaseous by-products.

Comparative Example 2:

Attempted Repeat of 2-Me-THF Dehydration using a Boron Phosphate Catalyst

The dehydration reaction in this example was performed in accordance with Comparative Example 1 except that the catalyst was regenerated prior to the run at 400° C. with an air flow of 128 SCCM for 16 hours. The furnace temperature was then adjusted to 350° C. and the carrier gas changed to nitrogen (80 SCCM). The performance of the catalyst is summarized in Table 1. This example shows that unlike the V—Ti—P catalyst, the boron phosphate catalyst either does not regenerate well or is deactivated from the prior run, or both. The 2-Me-THF conversion is markedly higher (98%) in this reaction but the selectivity to piperylene is less than 10%.

Comparative Example 3:

Dehydration of 2-Me-THF using a Boron Phosphate Catalyst

The catalyst used in this example was the same catalyst charge used in the previous example. The dehydration experiment was performed with the same reactor configuration as in the previous example but the catalyst was regenerated with 128 SCCM air flow at 400° C. for 16 hours. The reactor temperature was then set to 350° C., the 2-Me-THF feed rate set at 0.0759 mL/min and the nitrogen flow set to 0 SCCM. These reactor settings are the same as those discussed in the prior art on a per gram of catalyst basis. This example shows that the boron phosphate catalyst forms essentially no piperylene from 2-Me-THF when the reaction is carried out at the previously disclosed conditions, even though the conversion is 98%. The low material balance of 61% indicates extensive feed decomposition to coke or gaseous by-products. Indeed, the reactor tube was coated with dark deposits even after attempted regeneration. These results do not agree with those of the prior art which reports lower conversion but considerably higher selectivity to piperylene.

Example 5:

Dehydration of 3-methyl-tetrahydrofuran over the V—Ti—P Catalyst

The dehydration reaction in this example was carried out as described in Example 2 except that 3-methyl-tetrahydrofuran was used as the liquid feed. The catalyst used in this example was the same catalyst charge used in Example 4 but was regenerated with 128 SCCM air at 400° C. for 16 hours prior to use. The performance of the catalyst is summarized in Table 4. This example shows that the dehydration of 3-Me-THF is not as efficient as the corresponding 2-Me-THF reaction. The conversion was 58% and the selectivity to isoprene only 14%. Surprisingly, 1,3-pentadiene formed in 11% selectivity which indicates rearrangement of the substrate carbon skeleton.

Example 6:

Dehydration of n-pentanol over the V—Ti—P Catalyst

The dehydration reaction in this example was carried out as described in Example 5 except that n-pentanol was used as the liquid feed. The performance of the catalyst is summarized in Table 4. This example clearly demonstrates that the V—Ti—P catalyst is highly active and selective for n-pentanol dehydration, affording 100% conversion and 81% selectivity to pentene isomers.

Example 7:

Dehydration of 1,4-pentane diol over the V—Ti—P Catalyst

The dehydration reaction in this example was carried out as described in Example 5 except that 1,4-pentane diol was used as the liquid feed. The performance of the catalyst is summarized in Table 4. This example shows that although the substrate conversion is 100%, the selectivity to piperylene is less than 25%. Given that the substrate contains a highly reactive secondary alcohol, it is reasonable to assume that the reactor temperature was too high in this example. Lowering the reactor temperature is expected to increase the selectivity toward piperylene.

Example 8:

Dehydration of 1,5-pentane diol over the V—Ti—P Catalyst

The dehydration reaction in this example was carried out as described in Example 5 except that 1,5-pentane diol was used as the liquid feed. This example shows that the substrate was 100% converted with 34% selectivity to 1,3-pentadiene and 35% selectivity to the cyclic ether, tetrahydropyran (THP). Formation of the latter product is a reflection of partial dehydration of the substrate whereas the former product arises from complete dehydration.

Example 9:

Dehydration of tetrahydropyran over the V—Ti—P Catalyst

The dehydration reaction in this example was carried out as described in Example 5 except that tetrahydropyran was used as the liquid feed. The performance of the catalyst is summarized in Table 4. This example shows that THP is not as reactive as the other substrates screened. The conversion was 41% with the selectivity to piperylene being 45%.

Example 10:

Dehydration of 3-methyl-1,5-pentande diol over the V—Ti—P Catalyst

The dehydration reaction in this example was carried out as described in Example 5 except that 3-methyl-1,5-pentane diol was used as the liquid feed. This example shows that the substrate was converted in 100% with selectivity to 3-methyl-tetrahydropyran being 34% and selectivity to 3-methyl-1,3-pentadiene being 11%.

Example 11:

Dehydration of 2,5-hexane diol over the V—Ti—P Catalyst

The dehydration reaction in this example was carried out as described in Example 5 except that 2,5-hexane diol was used as the liquid feed. The performance of the catalyst is summarized in Table 4. This example shows that the substrate is converted in 100% with selectivity to hexadiene isomers being 45%. As noted it the above examples which employ substrates with secondary alcohols, the product selectivity in this example may also be higher upon lowering the reactor temperature.

Example 12:

Dehydration of Glycerol over the V—Ti—P Catalyst

The dehydration reaction in this example was carried out as described in Example 1 except that a thirty weight percent solution of glycerol in deionized water was used as the liquid feed and the reactor temperature was set to 250° C. Also, a fresh 5 g V—Ti—P catalyst charge was used and the biphasic product samples were homogenized with absolute ethanol rather than THF. The performance of the catalyst is summarized in Table 5. This example shows that the amount of glycerol converted was 37% while the selectivity to acrolein was 23%.

Example 13:

Dehydration of Glycerol over the V—Ti—P Catalyst at 275° C.

The dehydration reaction in this example was carried out as described in Example 2 except that the reactor temperature was set to 275° C. after catalyst regeneration. The performance of the catalyst is summarized in Table 5. This example shows that the amount of glycerol converted was 69% while the selectivity to acroelin was 60%.

Example 14:

Dehydration of Glycerol over the V—Ti—P Catalyst at 300° C.

The dehydration reaction in this example was carried out as described in Example 2 except that the reactor temperature was set to 300° C. after catalyst regeneration. The performance of the catalyst is summarized in Table 5. This example shows that the amount of glycerol converted was 92% while the selectivity to acroelin was 56%.

TABLE 1

Performance summary of 2-Me—THF dehydration over the V—Ti—P catalyst from Example 1-3 and Comparative Examples 1-3.

| Example | Mass Balance | Percent 2-Me—THF Converted | Percent Selectivity to 1,4-$C_5H_8$ | Percent Selectivity to 1,3-$C_5H_8$ | Percent Yield to Piperylenes | STY (mol 1,3-$C_5H_8$/Kg cat-h) |
|---|---|---|---|---|---|---|
| 1 | 93% | 60% | 9.6% | 60.1% | 42% | 8.6 |
| 2 | 94% | 88% | 5.5% | 66.4% | 63% | 14.0 |
| 3 | 93% | 88% | 65.5% | 66.3% | 63% | 14.0 |
| Comp. Ex. 1 | 77% | 62% | 0.8% | 25.2% | 16% | 5.9 |
| Comp. Ex. 2 | 61% | 98% | 0.3% | 8.2% | 8% | 1.81 |
| Comp. Ex. 3 | 57% | 92% | 0.0% | 0.7% | 0.6% | 0.1 |

TABLE 2

Weight percent GC analysis of reactor samples from Examples 1-3. Biphasic samples were homogenized by THF addition.

| | Example: 1 | | Example: 2 | | | Example: 3 | | |
|---|---|---|---|---|---|---|---|---|
| Sample Label: | Receiver | Trap 1 | Receiver | Trap 1 | Trap 2 | Receiver | Trap 1 | Trap 2 |
| Sample Weight (g): | 13.88 | 14.76 | 11.2 | 14.86 | 1.02 | 9.79 | 15.64 | 3.22 |
| Weight THF Added (g): | 34.06 | n/a | 39.49 | n/a | 3.77 | 35.28 | n/a | 12.65 |

TABLE 2-continued

Weight percent GC analysis of reactor samples from Examples 1-3.
Biphasic samples were homogenized by THF addition.

| | Example: 1 | | Example: 2 | | | Example: 3 | | |
|---|---|---|---|---|---|---|---|---|
| | \multicolumn{8}{c}{Sample Label:} | | | | | | | |
| | Receiver | Trap 1 | Receiver | Trap 1 | Trap 2 | Receiver | Trap 1 | Trap 2 |
| Total Sample Weight (g): | 47.94 | 14.76 | 50.69 | 14.86 | 4.79 | 45.07 | 15.64 | 15.87 |
| 1,4-Pentadiene (wt %): | 0.21 | 8.83 | 0.14 | 8.37 | 0.04 | 0.07 | 6.55 | 0.83 |
| trans-1,3-Pentadiene (wt %): | 1.83 | 33.35 | 1.61 | 44.08 | 0.64 | 1.21 | 49.97 | 7.43 |
| cis-1,3-Pentadiene (wt %): | 0.96 | 17.15 | 0.80 | 21.94 | 0.31 | 0.58 | 25.45 | 3.55 |
| THF (wt %): | 72.48 | 0.05 | 78.69 | 0.06 | 17.73 | 78.65 | 0.02 | 81.19 |
| 2-Me—THF (wt %): | 14.82 | 35.57 | 6.25 | 20.38 | 1.08 | 3.27 | 10.56 | 2.85 |
| 4-Penten-2-ol (wt %): | 0.05 | 0.03 | 0.03 | 0.06 | 0.00 | 0.00 | 0.05 | 0.00 |
| 3-Penten-2-ol (wt %): | 0.00 | 0.00 | 0.00 | 0.00 | 0.00 | 0.00 | 0.00 | 0.00 |
| 4-Penten-1-ol (wt %): | 0.16 | 0.01 | 0.12 | 0.00 | 0.00 | 0.07 | 0.00 | 0.00 |
| Unknowns Group1 (wt %): | 0.06 | 4.79 | 0.04 | 5.19 | 0.01 | 0.00 | 6.86 | 0.56 |
| Unknowns Group2 (wt %): | 1.79 | 1.50 | 2.29 | 4.32 | 0.16 | 1.39 | 4.23 | 0.83 |
| Total Wt %: | 92.36 | 101.28 | 89.97 | 104.40 | 19.97 | 85.24 | 103.69 | 97.24 |

TABLE 3

Performance summary of the lifetime study of 2-Me—THF dehydration over the V—Ti—P catalyst from Example 4.

| Time(h) | Mass Balance | Percent 2-Me—THF Converted | Percent Selectivity to 1,4-$C_5H_8$ | Percent Selectivity to 1,3-$C_5H_8$ | Percent Yield to Piperylenes | STY (mol 1,3-$C_5H_8$/Kg cat-h) |
|---|---|---|---|---|---|---|
| 2 | 66% | 95% | 3.3% | 47.0% | 48% | 10.7 |
| 4 | 94% | 80% | 6.8% | 74.6% | 66% | 14.4 |
| 6 | 92% | 70% | 7.0% | 70.0% | 55% | 11.8 |
| 8 | 94% | 61% | 7.7% | 70.7% | 48% | 10.3 |

TABLE 4

Performance summary of various substrate dehydrations over the V—Ti—P catalyst from Examples 5-11.

| Example | Organic Compound | Percent Conversion | Major Product | Percent Selectivity to Major Product | Minor Product | Percent Selectivity to Minor Product |
|---|---|---|---|---|---|---|
| 5 | 3-Me—THF | 53% | Isoprene | 14% | 1,3-Pentadiene | 10% |
| 6 | n-Pentanol | 100% | 1- & 2-Pentene | 71% | 2-Me-2-Butene | 10% |
| 7 | 1,4-Pentane diol | 100% | 1,3-Pentadiene | 21% | 1,4-Pentadiene | 2% |
| 8 | 1,5-Pentane diol | 100% | 1,3-Pentadiene | 34% | THP | 35% |
| 9 | Tetrahdropyran (THP) | 41% | 1,3-Pentadiene | 42% | 1,4-Pentadiene | 3% |
| 10 | 3-Methyl-1,5-pentane diol | 100% | 3-Me-THP | 34% | 3-Me-1,3-Pentadiene | 11% |
| 11 | 2,5-Hexane diol | 100% | 2,4-Hexadiene | 35% | 1,3- 1,4-, 1,5-Hexadiene | 10% |

TABLE 5

Performance summary of the effect of temperature on the V—Ti—P catalyzed dehydration of glycerol to acrolein.

| Example | Reactor Temperature | Mass Balance | Percent Glycerol Converted | Percent Selectivity to Acrolein | Percent Selectivity to Acetone | Percent Selectivity to Acetol | Percent Yield of Acrolein | STY (mol acrolein/Kg cat-h) |
|---|---|---|---|---|---|---|---|---|
| 12 | 250° C. | 97% | 37% | 23% | 0.1% | 0% | 8.5% | 0.6 |
| 13 | 275° C. | 98% | 69% | 60% | 2.5% | 12% | 41% | 3.2 |
| 14 | 300° C. | 94% | 92% | 56% | 1.8% | 7% | 52% | 4.0 |

The invention has been described in detail with particular reference to preferred embodiments thereof, but it will be understood that variations and modifications can be effected within the spirit and scope of the invention.

I claim:

1. A process for the dehydration of an oxygenated organic compound, comprising reacting the organic compound in the presence of a vanadium-titanium-phosphorus oxide catalyst to thereby dehydrate said organic compound to produce a diene,
   wherein the titanium component is a residue of a water-soluble organo-titanium compound comprising titanium (IV) bis(ammonium lactate)dihydroxide;
   wherein the oxygenated organic compound is selected from the group consisting of tetrahydrofuran, dihydrofuran, 1,2-cyclopentane diol, 1,3-cyclopentane diol, tetrahydropyran, dihydropyran, 2-methyl-tetrahydrofuran, 3-methyl-tetrahydrofuran, 2-methyl-tetrahydropyran, 3-methyl-tetrahydropyran, 1,2-cyclohexane diol, 1,3-cyclohexane diol, and 1,4-cyclohexane diol; and
   wherein the catalyst has the formula $VTi_aP_bO_c$, wherein a=0.3 to 6.0, b=2.0 to 13.0, and c is the number of atoms required to satisfy the valences of the components other than oxygen.

2. The process according to claim 1, wherein the organic compound is selected from the group consisting tetrahydrofuran, dihydrofuran, tetrahydropyran, dihydropyran, 2-methyl-tetrahydrofuran, 3-methyl-tetrahydrofuran, and 3-methyl-tetrahydropyran.

3. The process according to claim 1, wherein the process temperature is from about 250° C. to about 500° C.

4. The process according to claim 3, wherein the process temperature is from about 300° C. to about 450° C.

5. The process according to claim 4, wherein the process temperature is from about 325° C. to about 375° C.

6. The process according to claim 1, further comprising regenerating the catalyst between process runs in air at a temperature of from about 300° C. to about 600° C.

7. The process according to claim 1, wherein the pressure is from about 0.1 to about 100 bars absolute (bara).

8. The process according to claim 7, wherein the pressure is from about 1 to about 50 bara.

9. The process according to claim 8, wherein the pressure is from about 10 to about 20 bara.

10. The process according to claim 1, wherein the organic compound is selected from the group consisting of 2-methyl-tetrahydrofuran and 3-methyl-tetrahydrofuran.

\* \* \* \* \*